(12) United States Patent
Petersen et al.

(10) Patent No.: US 7,355,539 B2
(45) Date of Patent: Apr. 8, 2008

(54) MULTI-BIT ADC WITH SIGMA-DELTA MODULATION

(75) Inventors: Ethan Petersen, Castro Valley, CA (US); William Shea, Livermore, CA (US); Bradford B. Chew, San Ramon, CA (US)

(73) Assignee: Nellcor Puritan Bennett Inc., Pleasanton, CA (US)

( * ) Notice: Subject to any disclaimer, the term of this patent is extended or adjusted under 35 U.S.C. 154(b) by 0 days.

(21) Appl. No.: 11/604,589

(22) Filed: Nov. 27, 2006

(65) Prior Publication Data

US 2007/0132618 A1    Jun. 14, 2007

Related U.S. Application Data

(63) Continuation of application No. 10/787,542, filed on Feb. 25, 2004, now Pat. No. 7,142,142.

(51) Int. Cl.
    *H03M 3/00*    (2006.01)
(52) U.S. Cl. ........................ 341/143; 341/172
(58) Field of Classification Search ............. 341/143, 341/172, 118, 120
    See application file for complete search history.

(56) References Cited

U.S. PATENT DOCUMENTS

| | | | |
|---|---|---|---|
| 4,802,486 A | 2/1989 | Goodman et al. | |
| 4,851,841 A * | 7/1989 | Sooch | 341/143 |
| 4,911,167 A | 3/1990 | Corenman et al. | |
| 4,928,692 A | 5/1990 | Goodman et al. | |
| 4,934,372 A | 6/1990 | Corenman et al. | |
| 4,939,516 A * | 7/1990 | Early | 341/143 |
| 5,181,032 A * | 1/1993 | Ribner | 341/143 |
| 5,329,281 A * | 7/1994 | Baumgartner et al. | 341/139 |
| 5,351,685 A | 10/1994 | Potratz | |
| 5,368,026 A | 11/1994 | Swedlow et al. | |
| 5,621,408 A * | 4/1997 | Cake et al. | 341/143 |
| 5,662,106 A | 9/1997 | Swedlow et al. | |
| 5,685,301 A | 11/1997 | Klomhaus | |
| 5,713,355 A | 2/1998 | Richardson et al. | |
| 5,746,697 A | 5/1998 | Swedlow et al. | |
| 5,754,131 A | 5/1998 | Ribner et al. | |
| 5,803,910 A | 9/1998 | Potratz | |
| 5,815,102 A | 9/1998 | Melanson | |
| 5,907,299 A * | 5/1999 | Green et al. | 341/143 |
| 5,913,826 A | 6/1999 | Blank | |
| 5,921,921 A | 7/1999 | Potratz et al. | |
| 5,924,979 A | 7/1999 | Swedlow et al. | |

(Continued)

OTHER PUBLICATIONS

Partial International Search Report attached to PCT Invitation to Pay Additional Fees dated Jul. 21, 2005 (9 pages).

(Continued)

*Primary Examiner*—Linh Nguyen

(57) ABSTRACT

There is provided a pulse oximeter circuit including a feedback circuit configured to receive a digital output signal of a multi-bit sigma-delta modulator and generate a pulse width modulated signal (PWM). The PWM signal is directed to a first switching circuit and a D flip-flop. The first switching circuit provides a first or second reference voltage as a feedback signal to the multi-bit sigma-delta modulator. The D flip-flop generates a sample and hold signal. The sample and hold signal controls a second switching circuit coupled to the input of the multi-bit sigma-delta modulator.

20 Claims, 4 Drawing Sheets

U.S. PATENT DOCUMENTS

| | | | |
|---|---|---|---|
| 6,002,952 | A | 12/1999 | Diab et al. |
| 6,040,793 | A | 3/2000 | Ferguson et al. |
| 6,226,539 | B1 | 5/2001 | Potratz |
| 6,229,466 | B1 | 5/2001 | Gattani |
| 6,232,899 | B1 * | 5/2001 | Craven .................. 341/126 |
| 6,292,121 | B1 * | 9/2001 | Cake et al. ............. 341/143 |
| 6,340,945 | B1 | 1/2002 | Hauptmann et al. |
| 6,346,898 | B1 * | 2/2002 | Melanson ............... 341/143 |
| 6,360,113 | B1 | 3/2002 | Dettling |
| 6,445,302 | B2 * | 9/2002 | Vena ..................... 340/573.3 |
| 6,473,018 | B2 * | 10/2002 | Ueno et al. ............. 341/143 |
| 6,664,908 | B2 | 12/2003 | Sundquist et al. |
| 6,674,381 | B1 | 1/2004 | Gomez et al. |
| 2001/0030621 | A1 | 10/2001 | Matsumoto et al. |
| 2002/0128544 | A1 | 9/2002 | Diab et al. |

OTHER PUBLICATIONS

Anonymous: "PIC16C63A/65B/73B/74B—8-bit CMOS Microcontrollers with A/D Converter", Microchip Technology Inc., Article No. XP-002329893, retrieved from the internet URL:http://web.archive.org.web. 20030218133131/http://www 1.jaycar.com.au/images-uploaded/PIC16C63.PDF, pp. 1-184, no date.

S.R. Norsworthy, et al.: "A 14-bit 80-kHz Sigma-Delta A/D/ Converter: Modeling, Design, and Performance Evaluation", IEEE Journal of Solid-State Circuits, vol. 24, No. 2; Apr. 1, 1989; pp. 256-266.

Patent Abstracts of Japan, publication No. 62-159518, published Jul. 15, 1987 (2 pgs.).

* cited by examiner

_US 7,355,539 B2_

MULTI-BIT ADC WITH SIGMA-DELTA MODULATION

CROSS-REFERENCE TO RELATED APPLICATION

This application is a continuation of U.S. application Ser. No. 10/787,542 filed Feb. 25, 2004, now U.S. Pat. No. 7,142,142 the disclosure of which is hereby incorporated by reference in its entirety.

BACKGROUND OF THE INVENTION

The present invention relates to oximeters, and in particular to sigma-delta modulators used in connection with analog-to-digital conversion in pulse oximeters.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations accomplished by use of a non-invasive sensor which scatters light through a portion of the patient's tissue where blood perfuses the tissue, and photoelectrically senses the absorption of light at various wavelengths in such tissue. The amount of light absorbed is then used to calculate the amount of blood constituent being measured.

The light scattered through the tissue is selected to be of one or more wavelengths that are absorbed by the blood in an amount representative of the amount of the blood constituent present of the blood. The amount of transmitted light scattered through the tissue will vary in accordance with changing amount of blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photo-detectors sensitive to both of those wavelengths, in accordance with known techniques for measuring blood oxygen saturation.

Known non-invasive sensors include devices that are secured to a portion of the body, such as a finger, and ear or the scalp. In animals and humans, the tissue of these body portions is perfused with blood and the tissue surface is readily accessible to the sensor.

Typically, the analog-to digital conversion in a pulse oximeter is done using a sigma-delta modulator for analog-to-digital conversion after the signal is demodulated into the separate red and IR signals. An example of a pulse oximeter circuit using sigma-delta modulators is set forth in U.S. Pat. No. 5,921,921. The patent shows the use of two sigma-delta modulators, one for the red channel and one for the IR (infrared) channel. The sigma-delta modulators provide 1-bit of digital resolution, with the output of the sigma-delta modulator being filtered to produce a higher resolution signal. This is accomplished by using a fast oversampling rate (typically 1200 Hz) and then filtering to produce the slow, high resolution signal. The gain of the sigma-delta modulator in this patent is controlled by varying the width of the feedback pulse.

BRIEF SUMMARY OF THE INVENTION

The present invention moves the demodulator into the software domain, after the Analog-to-digital Converter (ADC). A sigma-delta modulator is used with a simple ADC. This allows the use of a single signal pat for the photo current signal, rather than demodulating into red and IR components as in the prior art, which required two ADCs. The red and IR signals are separated later, in the digital domain using a software or firmware program. By using the same hardware for both red and IR, there is no gain error introduced into one signal but not the other. Since the red and IR will have the same frequency response error, the calculation of blood oxygenation will cancel out this error. The demodulation in software also allows a more sophisticated demodulation scheme to be used.

The present invention is able to produce an accurate multi-bit ADC conversion with the sigma-delta modulator, rather than the single bit conversion of the prior art, by using a multi-bit feedback Digital-to-analog Converter (DAC) to provide a unique Pulse Width Modulated (PWM) feedback. The feedback DAC is clocked by a stable clock to provide a control output which controls a switch between two voltage references, which are added back into the input signal. The amount of time the high voltage reference is added in versus the amount the low voltage reference is added in provides a PWM signal to give an accurate analog feed back. The invention reduces linearity errors since the feedback is a function of a stable clock signal.

In another aspect of the invention, a switch at the input of the integrator used for the sigma-delta modulator provides a sample and hold circuit. An analog switch is used to switch between the non-inverting and inverting inputs of the operational amplifier of the integrator. The connection to the other input of the operational amplifier maintains the voltage of the input to switch at the same voltage level. A voltage reference is connected to this second input (e.g., the non-inverting input) to provide a source of sink for excess current, as needed.

In another aspect of the present invention, multiple capacitors are used for the integrator of the sigma-delta modulator. Different capacitors are switched in depending upon the input signal received. This allows a single sigma-delta modulator and ADC since a different capacitor can be dedicated to each signal to be demodulated. For example, a first capacitor can be used for a red signal and a second for the infrared signal. Additionally, third and fourth capacitors can be used for a first dark signal in between the red and infrared, or a second dark signal between the infrared and red. Thus, each capacitor stores the quantization error for a particular time slot, which allows the sigma-delta modulator ADC to operate on the signal before demodulation.

For a further understanding of the nature and advantages of the present invention, reference should be made to the following description taken in conjunction with the accompanying drawings.

DETAILED DESCRIPTION OF SPECIFIC EMBODIMENTS

Overall System

Figure 1:
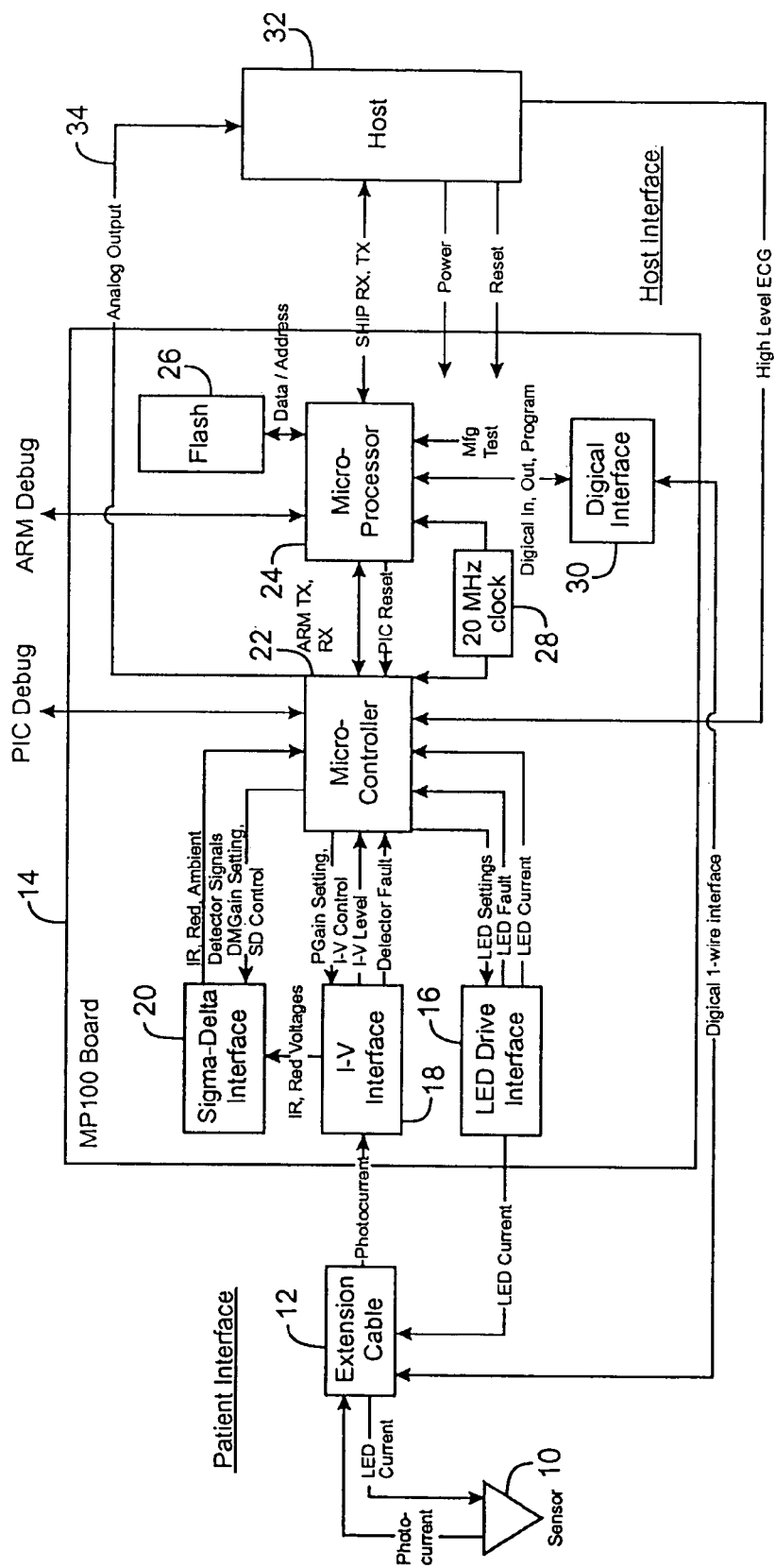
FIG. 1 is a block diagram of an oximeter incorporating the present invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22 which includes a 10 bit AD converter. Microcontroller 22 includes flash memory for a program, and RAM memory for data. The oximeter also includes a microprocessor chip 24 connected to a flash memory 26. Finally, a clock 28 is used and an interface 30 to a digital calibration in the sensor is provided. A separate host 32 receives the processed information, as well as receiving an analog signal on a line 34 for providing an analog display.

By using a sigma-delta modulator with the unique PWM feedback of the present invention, the simple, internal ADC of microcontroller 22 can be used an still provide the desired multi-bit precision. The ADC in this embodiment is a 10 bit successive approximation ADC. The precisely controlled PWM feedback connects in a voltage reference through switches 58 and 60, which are then summed in summing nodes with the input signal at the inputs of the integrators. The averages summed value, between the positive and negative reference voltages, provide the desired feedback. Any error is fed back in the following pulse period.

Sigma-delta Modulator

Figure 2:
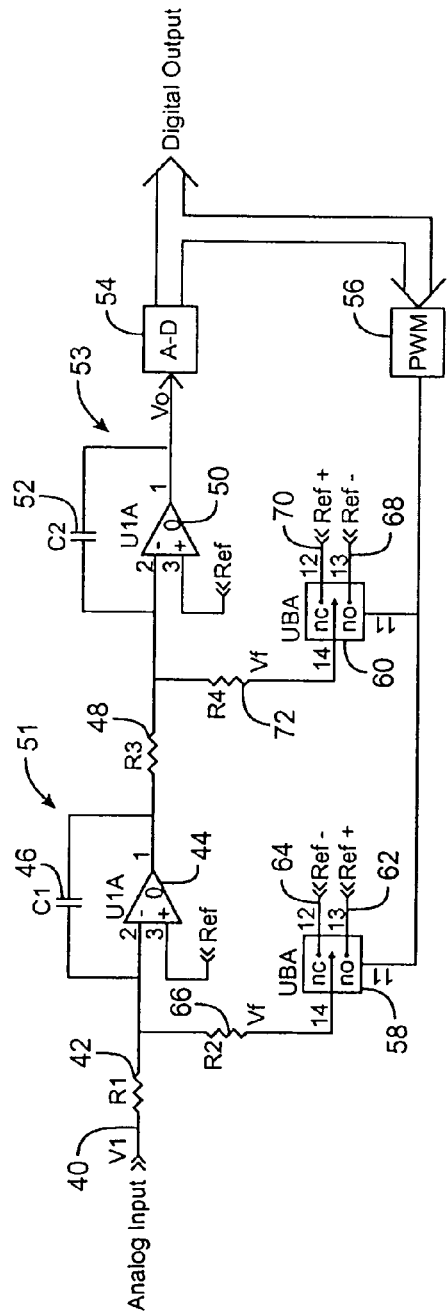
FIG. 2 is a circuit diagram of a two-stage sigma-delta modulator according to an embodiment of the invention.

FIG. 2 is a circuit diagram of a sigma-delta modulator according to an embodiment of the present invention, including portions of sigma-delta interface 20 and microcontroller 22 of FIG. 1. In particular, an analog input on a line 40 is provided through a resistor 42 to an inverting input of an operational amplifier 44 configured as an integrator 51 with a feedback capacitor 46. The non-inverting input is connected to a reference voltage (Ref). This is followed, through a connecting resistor 48, by a second operational amplifier 50, connected as an integrator 53 with a feedback capacitor 52. The output of operational amplifier 50 is connected to an analog-to-digital converter 54, which is the 10-bit A/D converter in microcontroller 22 of FIG. 1.

The digital output is fed back through a "digital-to-analog converter" 56 as a feedback circuit through a first switching circuit 58 and a second switching circuit 60. DAC 56 is internal to microcontroller 22, and produces the PWM output signal shown in FIG. 5. In response to the PWM control signal, switching circuit 58 alternately connects a positive or negative reference on lines 62 and 64 through a resistor 66 to connect with the input signal to the inverting input of operational amplifier 44. Similarly, second switching circuit 60 connects a negative and positive reference, inverted from the connections shown for switching circuit 58. These are reference voltages 68 and 70, which are connected through a resistor 72 to the inverting input of operational amplifier 50.

Figure 3:
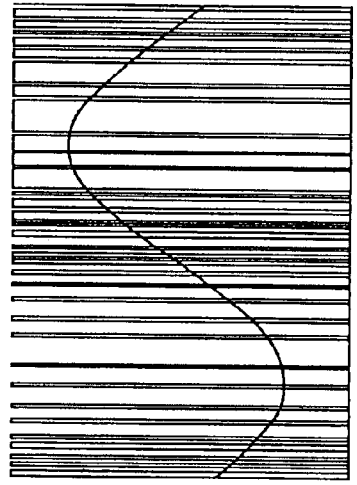
FIG. 3 is a diagram of a typical sigma-delta modulator output.

The feedback signal from digital-to-analog converter 56 is a pulse width modulated (PWM) signal, such as the typical signal shown in FIG. 3 for a sigma-delta modulator illustrating a sine waveform. By using a PWM signal and switching between only two voltages, the linearity of the feedback is a function of the clock signal. Since the clock signal is stable, and can be divided more accurately than the analog voltage, linearity errors are minimized. The multi-bit analog-to-digital converter, rather than the single bit converter of prior art devices, allows a more accurate result with a lower price sample rate. This eases the requirements for decimation filtering in software.

Sample and Hold

Figure 4:
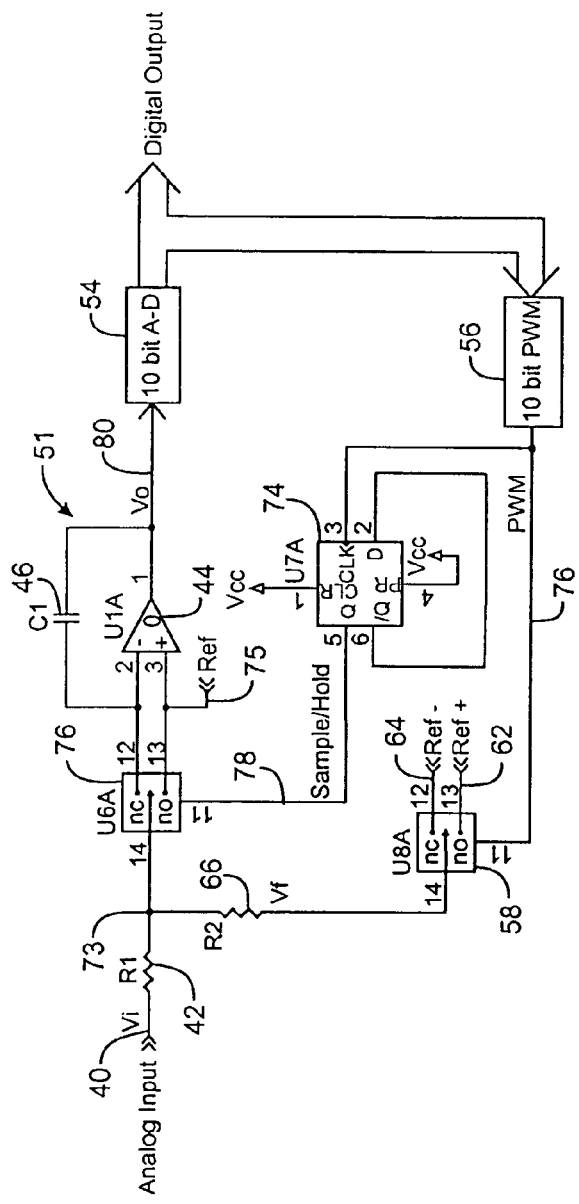
FIG. 4 is a circuit diagram of a sigma-delta modulator according to an embodiment of the present invention using the sigma-delta modulator for a sample and hold circuit with an analog switch to avoid charge injection.

FIG. 4 is a circuit diagram of an embodiment of the invention illustrating the switch controlling the input to the integrator in the sigma-delta modulator, with the switch being used for a sample of hold circuit. FIG. 4 shows many of the same circuit blocks as FIG. 2, such as analog-to-digital converter 54, feedback digital-to-analog converter 56, switching circuit 58, input resistors 42 and 66, and operational amplifier 44 configured as an integrator with capacitor 46. Only a single stage is shown for simplicity, and it is understood that an additional integrator 53 as in FIG. 2 could be added as well, with a similar switch for a sample and hold for the second integrator.

FIG. 4 adds a D flip-flop 74 and switching circuit 76. Switch 76 disconnects the input 40 from the input of operational amplifier 44 for a hold operation. When the input is reconnected after the sample has been held, a problem can arise since the voltage at the input can vary dramatically due to the feedback circuit through switch 58 and resistor 66. Since this feedback switches between a positive and negative voltage, a significant variation in the input voltage could occur. For example, the feedback might vary between approximately 0-3 volts, with the input being around 1 volt. This would result in a 1.5 volt swing. Such a swing would cause, upon reconnection to the inverting input of operational amplifier 44, a charge injection into capacitor 46, which is undesirable.

The present invention avoids such a charge injection by connecting the node 73 to the non-inverting input of operational amplifier 44. This non-inverting input further is connected to a reference voltage. This gives the current which would build up a place to go. The difference in voltage will result in current flow either toward or away from the reference voltage 75. Thus, upon reconnection, there will be minimal charge injection. The result of this structure is that the charge injection from the switch will be essentially constant, to the extent there is any, and it can be canceled out later by processing in a digital domain using a software or firmware program.

Figure 5:
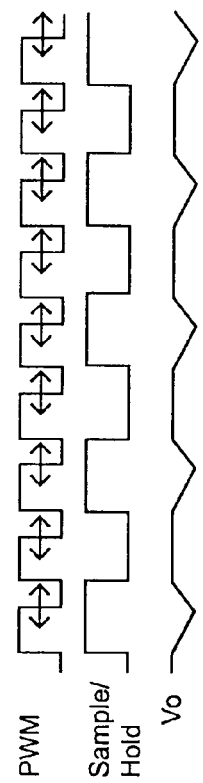
FIG. 5 is a timing diagram illustrating various signals of the circuit of FIG. 4.

FIG. 5 illustrates certain of the waveforms of the circuit of FIG. 4. The pulse width modified (PWM) signal on line 76 at the output of digital-to-analog converter 56 is shown first. The arrows signify that the width of the pulse will vary depending upon the signal. Next, the sample/hold signal on line 78 is shown, the non-inverting output of D flip-flop 74. Finally, the voltage out (Vo) signal on line 80 at the output of the integrator of operational amplifier 44 and capacitor 46 is shown. As can be seen, the Vo signal decays while the PWM signal is high, and increases or integrates while the PWM signal is low as long as the sample/hold signal is high, and increases or integrates while the PWM signal is low as long as the sample/hold signal is high. While the sample/hold signal is low, the Vo signal is held constant so that it can be sampled. Although illustrated at the same level each time in FIG. 5, the levels would vary with the amount of integration and the width of the pulse from the PWM feedback signal.

Multiple Capacitor Sigma-delta Modulator

Figure 6:
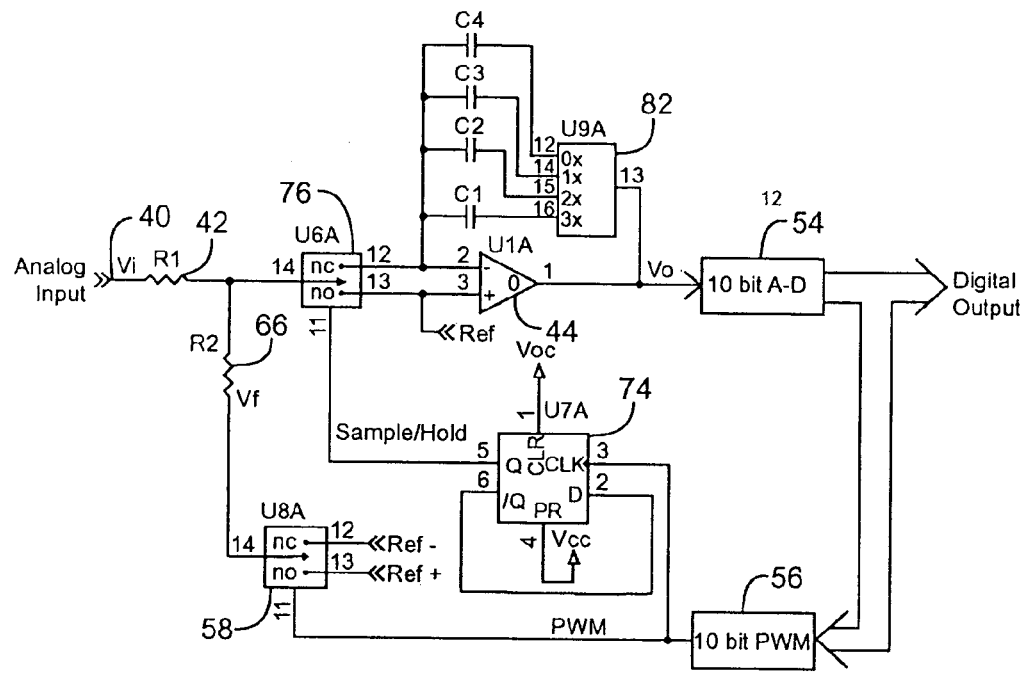
FIG. 6 is a circuit diagram of an embodiment of a sigma-delta modulator according to the present invention utilizing multiple capacitors in the integrator.

FIG. 6 illustrates a modification of the circuit of FIG. 4 in which capacitor 46 of FIG. 4 is replaced by one of four capacitors, C1, C2, C3, C4, which are selected by a switching circuit 82.

In a typical prior pulse oximeter, two separate integrators would need to be used with two separate signal paths and demodulation in the analog domain, so that the two different integrators could use two different capacitors for the red and IR signals. By instead switching in and out capacitors, a single integrator can be used, and the analog domain demodulation circuitry can be eliminated. Instead, the red and IR signals are time-multiplexed through the same integrator, with different capacitors being switched in for the red and IR signals. In addition, two additional capacitors can be added for the dark period in between the red and IR signals. Since the dark signal can very depending upon whether it follows the IR signal, or follows the red signal, two different capacitors can be provided to correspond to dark 1 and dark 2 signals. Thus, the present invention allows the demodulation of the signal to be moved into the digital domain and be done by a program in software or firmware, rather than having it done with hardware. This allows the hardware circuitry to be reduced in size by using only a single signal path, saving not only space and cost, but also power.

Figure 7:
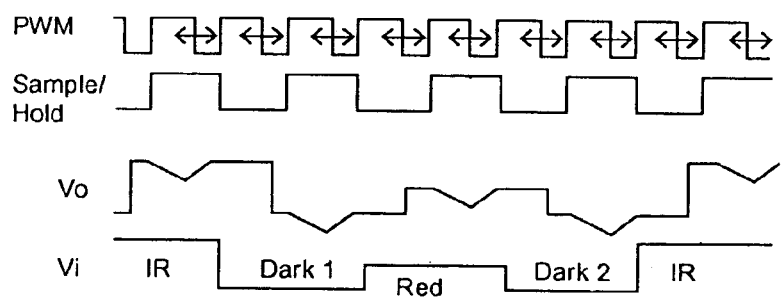
FIG. 7 is a timing diagram illustrating different signals of the circuit of FIG. 6.

FIG. 7 illustrates the different signals of FIG. 6, with the PWM, sample/hold, and $V_o$ signals as in FIG. 5, plus showing the voltage input ($V_i$) signal on input line 40. The PWM signal for the modulator has a fixed edge which occurs at a constant rate and can be used as a clock to synchronize the sampling of the modulator with the LEDs in the sensor, as will be discussed in greater detail below. The timing for the other edge is variable, as shown in FIG. 7, and allows for the amount of feedback to vary by controlling the switching of switching circuit 58.

In addition to controlling the switching circuit 58, the PWM signal is provided to the D flip-flop 74 which divides the PWM signal frequency by two to produce the sample/hold signal. The sample/hold signal is used to control switch 76 which enables or disables the input to the operational amplifier 44 by switching between the inverting and non-inverting inputs of the operation amplifier 44. As can be seen in FIG. 6, the operational amplifier 44 is configured to operate as an integrator circuit. When the switch 76 is coupled with the inverting input of the operational amplifier 44, current flows into the integrator circuit and the integrator circuit accumulates the total difference between the input signal and the feedback for that period. When the switch 76 couples to the non-inverting input, the current flow into the integrator circuit stops and the output (Vo) is held constant for measurement by the multi-bit ADC 54.

As the input line varies from IR to dark 1 to red to dark 2, switching circuit 82 switches between the different capacitors C1-C4. Specifically, after the ADC conversion is complete, the switch 82 switches to the capacitor holding the quantization error for the next sample period. The switching is controlled by a signal from the controller, since the controller knows when it switches on and off the red and IR LEDs, and thus can switch the capacitors at the same time[s]. The sample/hold signal allows time for the multi-bit ADC to make its conversion and the capacitors of the integrator to be switched. Any errors from the capacitor switching are allowed to settle out when the integrator is not sampling the signal and any errors from the LED drive switching are allowed to settle out when the integrator circuit is not switching.

In one embodiment, the features of FIGS. 2, 4, and 6 are combined, providing a two-stage integrator with PWM feedback, a switching circuit for each integrator to function as a sample and hold for the integrators, and multiple capacitors being switched in for each of the integrators. Thus, the present invention allows a single path to be used through the analog hardware circuitry for both red and the IR signals, saving components, cost, circuit size, and power consumption. By moving the demodulation from hardware into the digital domain to be done in software/firmware, there is no need to be concerned about mismatching of the filters for the red and IR signals, since the same filters are used. Since the accuracy of filtering in hardware is dependent upon component tolerance, using the same signal path allows the use of the same hardware, thus eliminating gain error introduced into one signal but no the other. If the red and IR signals have the same frequency response, the ratio-of-ratios (rat-rat) equation used by the software to calculate oxygen saturation will cancel out that error. Also, doing the demodulation in software allows a more sophisticated demodulation scheme to be used than what could be done easily in hardware.

As will be understood by those with skill in the art, the present invention may be embodied in other specific forms without departing from the essential characteristics thereof. For example, a third order modulator could be used, or a higher or lower resolution multi-bit analog-to-digital converter. Innumerable other variations could be made in the circuitry without departing from the essential characteristics of the invention. Accordingly, the foregoing description is intended to be illustrative of, but not limiting of, the scope of the invention which is set forth in the following claims.

What is claimed is:

1. A pulse oximeter circuit comprising:
a multi-bit sigma-delta modulator having an input adapted to receive a first analog signal representative of received red light and a second analog signal representative of received infrared light through a single path, the multi-bit sigma-delta modulator being configured to produce a digital output signal; and
a feedback circuit configured to receive the digital output signal of the multi-bit sigma-delta modulator and generate a pulse width modulated signal (PWM), the PWM signal being directed to a first switching circuit and a D flip-flop, the first switching circuit providing a first or second reference voltage as a feedback signal to the multi-bit sigma-delta modulator, the D flip-flop generating a sample and hold signal, the sample and hold signal controlling a second switching circuit coupled to the input of the multi-bit sigma-delta modulator, the second switching circuit being configured to direct the first and second analog signals to an inverting input of the multi-bit sigma-delta during a sampling period.

2. The pulse oximeter circuit of claim 1 comprising a multiple bit analog-to-digital converter coupled to the output of the multi-bit sigma-delta modulator to provide the digital output signal and wherein the feedback circuit includes a digital-to-analog converter having an input coupled to the digital output signal of the multi-bit sigma-delta modulator and being configured to generate the PWM signal.

3. The pulse oximeter circuit of claim 1 comprising:
a resistor coupled between the first switching circuit and the input of the multi-bit sigma-delta modulator.

4. The pulse oximeter circuit of claim 1 wherein the multi-bit sigma-delta modulator comprises:
an operational amplifier configured as an integrator circuit;
at least first and second capacitors; and
a capacitor switching circuit adapted to connect the first capacitor to the integrator upon receipt of the first analog signal and to connect the second capacitor to the integrator upon receipt of the second analog signal.

5. The pulse oximeter circuit of claim 4 comprising:
a third capacitor and a fourth capacitor, wherein the capacitor switching circuit is adapted to couple the third capacitor to the integrator during a first dark period and to couple the fourth capacitor to the integrator during a second dark period.

6. The pulse oximeter circuit of claim 1 wherein a single signal path through the multi-bit sigma-delta modulator is used for both the first analog signal representative of received red light and the second analog signal representative of received infrared light.

7. An oximetry device comprising:
a multi-bit sigma-delta modulator having an input adapted to receive a first analog signal from a sensor and a second analog signal from a sensor through a single path, the multi-bit sigma-delta modulator being configured to produce a digital output signal representative of the first and second analog signals;
at least first and second capacitors coupled in parallel to the input of the multi-bit sigma-delta modulator;
a capacitor switching circuit configured to couple to the first capacitor upon receipt of the first analog signal and to couple to the second capacitor upon receipt of the second analog signal, wherein the first and second capacitors are selected to correspond with a quantization error for the corresponding analog signals; and
a feedback circuit coupled about the multi-bit sigma-delta modulator, the feedback circuit comprising a sample and hold circuit configured to enable the input of the multi-bit sigma-delta modulator during receipt of the first or second analog signals and to disable the input during a holding period.

8. The oximetry device of claim 7 wherein the first analog sensor signal is representative of received red light, and the second analog sensor signal is representative of received infrared light.

9. The oximetry device of claim 7 wherein the feedback circuit comprises a digital-to-analog converter configured to produce a pulse width modulated (PWM) signal.

10. The device of claim 9 wherein the feedback circuit comprises a reference voltage switch controlled by the PWM signal.

11. The oximetry device of claim 9 wherein the PWM signal is provided to the sample and hold circuit, the sample and hold circuit being configured to divide the PWM signal by two to produce a sample/hold signal.

12. The oximetry device of claim 7 wherein the sample and hold circuit comprise a D flip-flop and a switching circuit, the switching circuit being configured to alternately couple to an inverting input and a non-inverting input according to a sample/hold signal generated by the D-flip-flop.

13. The oximetry device of claim 7 comprising a signal processor adapted to demodulate the digital output signal produced by the multi-bit sigma-delta modulator into a first digital signal representative of the first analog signal and a second digital signal representative of the second analog signal.

14. The oximetry device of claim 13 comprising a memory coupled with the signal processor, the memory containing a program adapted to demodulate the digital output signal produced by the multi-bit sigma-delta modulator into the first digital signal representative of the first analog signal and the second digital signal representative of the second analog signal.

15. A method for analog-to-digital conversion comprising:
converting a digital output signal of a multi-bit sigma-delta modulator to an analog pulse width modulated (PWM) signal, the PWM signal having one fixed edge occurring at a constant rate and one variable edge;
controlling a feedback circuit using the PWM signal to provide a first or second reference voltage as a feedback signal;
generating a sample/hold signal by dividing the PWM signal, the sample/hold signal controlling an input switch of the multi-bit sigma-delta modulator;
combining the feedback signal through a resistor with first and second analog signals to generate a combined signal, the first and second analog signals representing a detected red signal and a detected infrared signal; and
alternately coupling the combined signal to an inverting input or a non-inverting input of an operational amplifier of the multi-bit sigma-delta modulator to provide sampling periods or holding periods, respectively.

16. The method of claim 15 comprising:
coupling a first capacitor about the operational amplifier to sample the first analog signal during a during a first sampling period; and
converting the sampled first analog signal to a digital signal using an analog-to-digital converter to generate a digital output during a first holding period.

17. The method of claim 16 comprising:
switching from the first capacitor to a second capacitor after the first analog signal has been converted to a digital signal;
sampling the second analog signal during a second sampling period; and
converting the sampled second analog signal to a digital signal using an analog-to-digital converter to generate a digital output during a second holding period.

18. The method of claim 17 comprising:
coupling a third capacitor about the operational amplifier during a dark period occurring immediately after the first holding period; and
coupling a fourth capacitor about the operational amplifier during a dark period occurring immediately after the second holding period.

19. The method of claim 15 comprising processing the digital output signal to separate the digital output signal into a first digital signal representing the first analog signal and a second digital representing the second analog signal.

20. The method of claim 19 comprising determining physiological parameters using the first and second digital signals.

* * * * *